United States Patent [19]

Sinclair et al.

[11] Patent Number: 5,737,061
[45] Date of Patent: Apr. 7, 1998

[54] METHODS FOR DIAGNOSING BOVINE SPONGIFORM ENCEPHALOPATHY

[75] Inventors: Robert Sinclair, Mendham, N.J.; Leonard Scinto, Cambridge, Mass.

[73] Assignee: Applied Science Group, Inc., Bedford, Mass.

[21] Appl. No.: 658,813

[22] Filed: Jun. 7, 1996

[51] Int. Cl.$^6$ .............................. A61B 3/00; A01N 43/04
[52] U.S. Cl. ............................. 351/246; 514/54
[58] Field of Search .................................. 351/200, 246, 351/204; 514/54, 885, 23

[56] References Cited

PUBLICATIONS

Editorial, "Less Beef, more brain" The Lancet 347:915, 1996, no month.
Will et al. "A new variant of Creutzfeldt–Jakob disease in the UK" The Lancet 347:921–925, 1996, no month.
Tabrizi, "Creutzfeldt–Jakob disease in a young woman" The Lancet 347:945–949, 1996, no month.
Chazot et al., "A New Variant of Creutzfeldt–Jakob disease in a 26–year–old French man" The Lancet 347:1181, 1996, no month.
Collinge and Rossor, "A New Variant of Prion Disease" The Lancet 347:916–917, 1996, no month.
Collee, "A dreadful Challenge" The Lancet 347:917–918, 1996, no month.

*Primary Examiner*—Hung X. Dang
*Attorney, Agent, or Firm*—Fish & Richardson P.C.

[57] ABSTRACT

The invention features a non-invasive method for diagnosing bovine spongiform encephalopathy in a mammal, e.g., a cow. The method entails measuring changes in pupil area in response to a neurotransmitter agonist or antagonist applied to the eye.

2 Claims, No Drawings

METHODS FOR DIAGNOSING BOVINE SPONGIFORM ENCEPHALOPATHY

FIELD OF THE INVENTION

The present invention is concerned with non-invasive methods for the diagnosis of bovine spongiform encephalopathy in cattle. In particular, the invention is directed to diagnostic methods involving the measurement of changes in pupillary dilation or constriction caused by the application of certain neurotransmitter agonists or antagonists to the eye of a cow.

BACKGROUND OF THE INVENTION

Bovine spongiform encephalopathy (BSE) is a severe neurological disease afflicting domestic cattle in the United Kingdom, France, Portugal, Republic of Ireland, Switzerland, and elsewhere. Since 1986, more than 150,000 cases of BSE have been confirmed in the U.K. alone. BSE is fatal for cattle within weeks to months of its onset.

BSE is associated with a transmissible agent, the precise nature of which is poorly understood. The transmissible agent is very stable, resisting heating at temperatures normally used for sterilization. The infectious agent in BSE is almost certainly a prion. Prions are proteinaceous infectious particles which are resistant to inactivation by procedures that modify or destroy nucleic acids. It is thought that prions cause infection via transfer of a protein, without the transfer of nucleic acid. The mechanism by which a protein can act as an infectious agent is a matter of considerable debate. It is possible that a prion is a disease-causing, variant form of a normal, naturally occurring protein. The variant form may be able to cause a structural change in the normal protein, converting it into the disease-causing, variant form.

Several other prion diseases have been identified, including: scrapie in sheep, transmissible mink encephalopathy in mink, and chronic wasting disease in mule deer and elk. It is widely believed that the incorporation of parts of sheep infected with scrapie in to commercial cattle feed was the source of BSE in domestic cattle.

Recently, considerable concern has arisen over the possibility of a link between BSE and Creutzfeldt-Jakob disease (CJD), a severe neurological disorder afflicting humans. Like BSE, CJD is thought to be caused by a prion. The recent observation in the U.K. of 10 cases of a new, variant form of CJD suggests the presence of a new risk factor. While no direct link between CJD and BSE has been found, there is considerable concern that the variant form of CJD may be caused by consumption of BSE contaminated beef. In early 1996, The United Kingdom Advisory Committee on Spongiform Encephalopathy, referring to this variant form of CJD, concluded that "although there is no direct evidence of a link on current data and in the absence of any credible alternative, the most likely explanation at present is that these cases are linked to exposure to BSE before the introduction of the specified bovine offal ban in 1989." After undertaking a study of the possibility of a link between the new variant form of CJD and BSE, the World Health Organization recommended that no part of any animal that has shown signs of BSE should enter the food chain.

Presently, BSE is commonly diagnosed by observing the cow for signs of behavioral symptoms of the disease, e.g., an unsteady gait or excessive nose licking. There is a need for additional methods for identifying cattle afflicted with BSE.

SUMMARY OF THE INVENTION

The present invention provides non-invasive methods for diagnosing bovine spongiform encephalopathy (BSE) in cattle. The methods of the invention are based, in part, on the discovery that the response of BSE afflicted animals to certain neurotransmitters agonists and antagonists applied to the eye differs from that of non-afflicted animals.

In the methods of the invention, the size of the pupil of the treated eye is measured during at least two different periods: a baseline measurement period and a test measurement period. During each period, which can last from less than one second to several seconds, numerous measurements of pupil size can be made. The multiple measurements made in each measurement period can then be separately averaged to establish an average baseline measurement and an average test measurement.

The baseline measurements can be made by measuring the pupil of the untreated eye, measuring the pupil of the treated eye before administration of the neurotransmitter agonist or antagonist, or measuring the pupil of the treated eye after treatment, but before any significant change in pupil size caused by the treatment could reasonably occur. Thus, the baseline measurement period can occur before or after administration of the selected neurotransmitter agonist or antagonist to the treated eye.

The test measurement period occurs after administration of the neurotransmitter agonist or antagonist to the treated eye at a time when the change in pupil size induced by the particular neurotransmitter agonist or antagonist employed can be observed in cows afflicted with BSE and distinguished from the change induced in non-afflicted cows. The pupil size established during the test measurement period is compared to the pupil size established during the baseline measurement period.

Because BSE afflicted cows are more sensitive to the effects of certain neurotransmitter agonists and antagonists administered to the eye then are non-afflicted animals, the effect of the neurotransmitters on pupil size can be used to diagnose BSE.

There is a positive BSE diagnosis in the method of the invention when the pupillary dilation induced by a given dose of a selected mydriatic agent is greater than that generally induced by similar treatment in a cow which is not afflicted with BSE or when the pupillary constriction induced by a given dose of a selected miotic agent is greater than that generally induced by similar treatment in a cow which is not afflicted with BSE. Thus, the difference between the test measurement pupil size and the baseline measurement pupil size is compared to the difference generally observed in cows not afflicted with BSE which have been similarly treated.

An understanding of the following terms is useful for understanding certain aspects of the methods of the invention.

Cholinergic: A term pertaining to the neural transmitter acetylcholine. The term is particularly used to designate nerve fibers that release acetylcholine at their terminals, or the physiological effects produced by the stimulation of these nerve fibers, or the acetylcholine receptors on the post synaptic membrane, or chemical agents and drugs that imitate the effects of acetylcholine.

Adrenergic: A term designating activation by, characteristic of, or a secreting of the neural transmitter epinephrine or substances with similar epinephrine-like activity. The term is also used to refer to those postganglionic sympathetic nerve fibers that liberate norepinephrine in response to a nerve impulse; and is typically used to identify an agent that produces such an effect.

Mydriasis: Dilation of the pupil.

Mydriatic agent: A compound or substance which initiates, induces, promotes or causes pupil dilation.

Miosis: Constriction of the pupil.

Miotic agent: A compound or substance with initiates, induces, promotes, or causes pupil constriction.

Neurotransmitter (also Neurotransmitter and Synaptic Transmitter): A compound or substance that serves to transmit a nerve impulse between cells at a synapse or a neuromuscular junction. Such compounds include but are not limited to acetylcholine, epinephrine, norepinephrine, dopamine, serotonin, γ-aminobutyric acid, glycine, and glutamate.

Constriction Velocity: The average rate of change in pupil area expressed in mm/sec over a given interval of time from initial size to maximal constricted size of pupil.

Re-dilation velocity: The rate of recovery expressed as mm/sec to maximal resting pupil area after stimulation by light.

Endogenous substance: A compound or composition synthesized, found, or originating outside the person's body.

Photostimulation (visible light stimulation): The purposeful introduction of visible light energy to the eye of a living subject.

Light energy (photoenergy): Electromagnetic radiation of any wavelength including infrared, visible and ultraviolet wavelengths.

Agonist: A compound or substance that imitates, mimics, or acts in a manner similar to the activity or function of a specified tissue, composition or agent.

Antagonist: A compound or substance that blocks the activity or function of a specified tissue, composition or agent.

Mediator: A compound, composition, agent or substance that influences, effects, intervenes, contradicts, mitigates, modifies, promotes, or is involved with an activity or function in a specified manner.

Velocity: The rate of change of size or rate of displacement typically expressed in units (e.g., millimeters per second). Velocity is a vector quantity and a complete specification which states both the direction as well as the magnitude of change.

DETAILED DESCRIPTION OF THE INVENTION

The present invention is directed to non-invasive methods for diagnosing BSE in cattle. The methods of the invention are based, in part, on the discovery that BSE afflicted animals are hypersensitive to certain neurotransmitter agonists and antagonists administered to the eye.

In the methods of the invention, the size of the pupil of the treated eye is measured during at least two different periods: a baseline measurement period and a test measurement period. During each period, which can last from less than one second to several seconds, numerous measurements of pupil size can be made. The multiple measurements made in each measurement period can then be separately averaged to establish an average baseline measurement and an average test measurement.

The baseline measurements can be made by measuring the pupil of the untreated eye, measuring the pupil of the treated eye before administration of the neurotransmitter agonist or antagonist, or measuring the pupil of the treated eye after treatment, but before any significant change in pupil size caused by the treatment could reasonably occur. Thus, the baseline measurement period can occur before or after administration of the selected neurotransmitter agonist or antagonist to the treated eye.

The test measurement period occurs after administration of the neurotransmitter to the treated eye at a time when changes in pupil size induced by the particular neurotransmitter agonist or antagonist employed can be observed in cows afflicted with BSE and distinguished from the change in pupil size induced by similar treatment of cows not afflicted with BSE. The pupil size established during the test measurement period is compared to the pupil size established during the baseline measurement period.

The preferred methods for determining whether an animal is afflicted with BSE entails measuring pupil size, preferably using an automated device such as a pupillometer. Because the pupils of cows are roughly rectangular rather than round, diameter of the pupil is not a relevant measure of pupil size. Instead it is preferred that the total area of the pupil or the height of the pupil be measured. Pupil height is a useful measurement because, unlike pupil width, pupil height is influenced by the topical administration neurotransmitter agonists and antagonists. Thus, where measurement pupil size is referred to, it should be understood that pupil area or pupil height can be measured.

The methods of the invention have several advantages, including the following:

1. The diagnostic methods of the invention are relatively non-invasive.

2. The diagnostic methods of the invention can employ automated equipment to repetitively measure pupil size over time and cumulatively record such data as it is obtained. The data collected can be analyzed to provide a quantitative results for comparison with established ranges of normal and abnormal values. In this manner, a reliable determination can be made as to whether or not a particular animal is afflicted with BSE.

3. The diagnostic methods can be performed relatively easily and can be completed rapidly. The data can be printed, displayed on a monitor, or transferred to a remote reference facility for final analysis.

As noted above, the test measurement period should occur when the change in pupil size induced by the particular neurotransmitter agonist or antagonist employed can be observed in cows afflicted with BSE and differs from the change in pupil size induced by similar treatment of cows not afflicted with BSE. Preferably, but not necessarily, the test measurement period occurs when the difference between the pupil size change induced in BSE afflicted cows and cows not afflicted with BSE is maximal or near maximal. The time at which differences can be observed will depend on the identity of the neurotransmitter agonist or antagonist used and its dosage. Those skilled in the art can empirically determine, for each particular neurotransmitter agonist or antagonist employed, the appropriate time after treatment at which to make test measurements. This can be done by carrying out a series of measurements on a small number of BSE afflicted cows and non-afflicted cows and identifying the point in time after treatment when there is a consistent, measurable difference in pupil size between treated BSE afflicted cows and treated cows not afflicted with BSE. Once one has determined a preferred time after administration of a particular neurotransmitter agonist or antagonist for the making of test measurements, one can reliably use this time in any diagnostic setting using the same neurotransmitter agonist or antagonist at the same dosage.

Of course, it is possible to include two or more baseline measurement periods and/or two or more test measurement periods. It is sometimes possible to obtain a more reliable diagnosis by including more than one test measurement period. In particular, by including several test measurement periods, one is more likely to take measurements at the time when the difference in the response of BSE afflicted cows and non-afflicted cows is maximal or near maximal.

Because pupil size is influenced by the level of light striking the pupil, the level of light striking the pupil should be the same during both the baseline measurement period and the test measurement period. It is important that the pupils of the animal being tested have an opportunity to adjust to the light level before each measurement period. Preferably, when an agent causing dilation is used, the light level at the pupils is high so that the pupils are maximally constricted or nearly so. Similarly, when an agent causing constriction is used, the light level at the pupils is low so that the pupils are maximally dilated or nearly so. This arrangement permits one to more readily observe changes in pupil size induced by the agent used. Thus, when using cholinergic agonists or adrenergic antagonists—agents which cause pupillary constriction, the lighting should be low so that the animal's pupils are dilated prior to treatment. In contrast, when using cholinergic antagonists or adrenergic agonists—agents which cause pupillary dilation, the lighting should be high so that the animal's pupils are constricted prior to treatment.

Diagnosis of BSE Based Upon Neurotransmitter-Stimulated Changes in Pupil Area

BSE can be diagnosed either by assessment of an animal's response to a neurotransmitter agonist or antagonist which can cause pupil dilation when administered topically to the eye or by assessment of an animal's response to a neurotransmitter agonist or antagonist which can cause pupil constriction when administered topically to the eye.

Pupil Dilation (Mydriasis)

In the method of the invention pupil dilation can be triggered by administering to an eye of the animal a dilute solution of a neurotransmitter agonist or antagonist which is a recognized and conventionally known mydriatic agent. Typically this will be an agent selected from the group consisting of cholinergic antagonists, adrenergic agonists, or a combination of these agents. A representative, but not exhaustive, listing of these drugs is provided in Table 1 below, along with the dosage commonly used in humans.

The dosage of a given mydriatic agent which induces dilation in humans can be a useful starting point for determining a suitable dosage for use in the method of the invention. In using human dosages for guidance, the permeability of the bovine eye relative to the human eye is preferably taken into account. The appropriate diagnostic dosage should be empirically determined. The standard reference work "The Pupil" (Loewenfeld, Iowa State University Press, Ames, Ind.) provides considerable information concerning the use of mydriatic agents in humans, including dosages which induce dilation.

TABLE 1

| Mydriatic Agents | |
|---|---|
| | Conventional Dosage in Humans |
| A. Anticholinergic Agents | |
| Tropicamide | 0.5–1.0% |
| Atropine | 1% |
| Homotropine Hydrobromide | 2% |
| Cyclopentolate Hydrochloride | 0.5–2% |

TABLE 1-continued

| Mydriatic Agents | |
|---|---|
| | Conventional Dosage in Humans |
| Scopolamine | 0.2–0.25% |
| B. Adrenergic Agents | |
| Phenylephrine Hydrochloride | 2.5% |
| Hydroxyampheamine Hydrobromide | 1% |
| Dipivefrin | 0.1% |
| Epinephrine | 1–2% |
| C. Combined Agents | |
| Cyclopentolate Hydrochloride/ Phenylephtine phenylephtine | 0.2% cyclopentolate/1% |

Pupil Constriction (Miosis)

Pupil constriction can be triggered by the administering to the eye of the animal a dilute solution of a miotic agent. Miotic agents are cholinergic agonists or adrenergic antagonists. The agents include the classes of parasympathetic agents, short-acting anticholinesterase agents, and long-acting anticholinesterase agents. A representative, but non-exhaustive, listing is provided in Table 2 below, along with the dosage commonly used in humans.

The dosage of a given miotic agent which induces pupillary constriction in humans can be a useful starting point for determining a suitable dosage for use in the method of the invention. In using human dosages for guidance, the permeability of the bovine eye relative to the human eye is preferably taken into account. The appropriate diagnostic dosage should be empirically determined. The standard reference work "The Pupil" (Loewenfeld, Iowa State University Press, Ames, Ind.) provides considerable information concerning the use of miotic agents in humans, including dosages which induce pupillary constriction.

TABLE 2

| Miotic Agents | |
|---|---|
| | Conventional Dosage in Humans |
| A. Parasympathomimetic Agents | |
| Pilocarpine Hydrochloride | 14% |
| Pilocarpine Nitrate | — |
| Carbachol | 0.75–3% |
| B. Short-Acting Anticholinesterase Agents | |
| Physostigmine Sulfate | 0.25% |
| Physostigmine Salicylate | — |
| C. Long-Acting Anticholinesterase Agents | |
| Demecarium Bromide | 0.125–0.25% |
| Echothiophate Iodide | 0.03–0.6% |
| D. Beta-Adrenergic Antagonists | |
| Timolol Maleate | 0.25–0.5% |

General Guidelines for Practicing the Diagnostic Method

The following general guidelines are meant to be illustrative, not limiting. Those skilled in the art will be able to optimize the parameters of used for particular agents and test conditions.

1. Duration of the Measurement Period

Pupil size is preferably measured using a non-invasive automated apparatus to continuously monitor and repetitively measure pupil size over time for a pre-chosen duration ranging from less than 1 second to about 5 minutes (300 seconds). Each continuous observation and repeated determination of pupil size over time constitutes one "measurement period." Preferably, the automated apparatus is able to monitor and measure pupil size repeatedly and continuously at a rate of at least 60 determinations per second. However, automated apparatuses which perform takes measurements at a slower rate (e.g., less than 20 determinations per second) can also be used. It is also possible to measure pupil size without the use of automated equipment. For example, pupil size can be measured directly using a ruler or indirectly from photographs.

It will be readily recognized that the amount of data available for analysis will increase as the duration of the measurement period increases. Thus, for data obtained at a rate of 60 determinations per second, a one second measurement period yields 60 individual measurements of pupil size whereas a sampling period of 30 seconds would yield 1800 individual measurements of pupil size, with the entire 30 second interval constituting one measurement period. Thus, longer measurement periods produce more data for subsequent analysis.

The present invention requires that sufficient data be obtained to provide a statistically meaningful measure of pupil size. If the total number of individual measurements is too low, the diagnosis will be less reliable.

The present methodology allows for a choice in the duration of time constituting one "measurement period." The duration of the measurement period is preferably reasonably constant during the entire diagnostic protocol. The measurement period need not be a single uninterrupted period of measurement. Instead, a measurement period can be divided into a number of discrete sub-periods separated by a few seconds or longer.

The duration of the measurement period and the frequency of measurement during the measurement period can be selected by one skilled in the art. These parameters should be selected so that the total number of measurements are sufficient to yield a diagnosis having the desired degree of accuracy.

2. Number of Measurement periods

Preferably, at least two measurement periods, separated by a selected length of time, are used in the method of the invention. One measurement period provides the initial baseline characteristics of untreated pupil size for the individual animal. One or both eyes can be measured to establish a baseline.

In general, either of the two eyes may be used as the targeted eye for subsequent treatment with the selected neurotransmitter agonist or antagonist. Sterile saline is preferably administered to the control eye.

After performing the baseline measurement, the present diagnostic method requires that at least a second measurement period occur, preferably at a time when the maximum difference in pupil size between BSE afflicted cows and cows not afflicted with BSE occurs. The method therefore requires at least two different measurement periods of specified duration during which the treated targeted eye and, preferably, the non-treated control eye are monitored and measured.

3. Concentration of the Chosen Neurotransmitter Agonist or Antagonist

The concentration of neurotransmitter agonist or antagonist used should be such that it will not preferably not substantially affect the pupillary response of animals which are not afflicted with BSE.

Depending on the concentration of neurotransmitter agonist or antagonist actually used, the amount of time before the most significant difference in pupillary response between BSE afflicted animals normal controls may differ. Thus, the time at which the test measurements are made will vary.

It will also be appreciated that the method can employ a concentration of neurotransmitter agonist or antagonist which is sufficient to cause a noticeable change in pupil size and pupillary response even in a normal animal, provided that the response in BSE afflicted animals is greater, e.g., a greater difference in dilation or constriction or longer lasting dilation or constriction.

4. Preferred Basis for Comparing the Empirically Obtained Result in Order to Diagnose BSE Diagnosis is preferably made when the change in the size of the pupil of the eye treated with the selected neurotransmitter agonist or antagonist exceeds a predetermined range of numerical values representative of a population of animals not afflicted with BSE. This range of numerical values is considered the diagnostic criterion for determining the presence or absence of BSE in an animal. The diagnostic evaluation is empirically determined by examining the percentage change in pupil size for diagnosed BSE afflicted animals and for non-afflicted animals for a particular neurotransmitter agonist or antagonist at a particular concentration and determining the point at which known BSE afflicted animals and non-afflicted animals are distinguishable.

Preferred Protocols

It will be appreciated that the preferred protocols presented herein are merely illustrative of the diagnostic methodology as a whole and are intended to be modified by those skilled in the art so as to accommodate different automated equipment and test conditions.

The preferred protocols utilize a neurotransmitter agonist or antagonist which causes pupillary dilation.

First Preferred Protocol a) Allow several minutes for the animal's pupils to adjust to ambient illumination.

b) Image one eye of the animal with a suitable pupil measurement instrument to obtain a baseline measurement. If desired, the pupil of the other eye may also be measured.

c) After completing the baseline measurements, administer the chosen neurotransmitter agonist or antagonist at the appropriate use concentration (e.g., 400 μl of a 0.5% tropicamide solution) to one targeted eye, chosen arbitrarily.

d) Allow the eye to adjust to ambient illumination and proceed to image the pupil as described in b) above.

e) Repeat the procedure in steps c) and d) with the non-treated eye using a single drop of sterile water for ophthalmic use in the place of the chosen neurotransmitter agonist or antagonist.

f) After a period selected to distinguish be afflicted and non-afflicted animals has elapsed, measure the pupil of the treated eye and the untreated eye Second Preferred Protocol a) Allow several minutes for the animal's pupils to adjust to ambient illumination.

b) Image one eye of the animal with a suitable pupil measurement instrument. This will be the baseline measurement.

c) After completing the baseline measurements, administer an appropriate amount of the chosen neurotransmitter agonist or antagonist at an appropriate concentration to one targeted eye chosen arbitrarily.

d) Allow the eyes to adjust to ambient illumination and image the treated eye.

e) Repeat the procedure in steps c) and d) with the other eye (non-treated eye) but using a single drop of sterile water for ophthalmic use instead of the neurotransmitter agonist or antagonist.

f) After administration of the sterile water to the non-treated eye, measure the pupil of the non-treated eye using a suitable measurement instrument.

g) Repeat measurement cycle every few minutes up to the time at which maximal differences between BSE afflicted and non-afflicted animals are observed for the particular drug and drug concentration used.

Experimental Results

In the first series of experiments, 500–600 μl of 1% tropicamide was introduced into one eye of several healthy cows and several cows suffering from BSE. The pupils of all of the animals were examined before and after treatment. Prior to administration, the pupils of all animals were approximately 0.5 cm high. Approximately 30 to 40 minutes after administration of tropicamide, the treated pupils of healthy and BSE-afflicted cows were observed to be dilated. After several hours, the treated pupils of healthy cows had returned to approximately their original size, while the treated pupils of BSE-afflicted cows remained somewhat dilated.

In the next series of experiments, 400 μl of 0.5% tropicamide was introduced into one eye of several healthy cows and several cows suffering from BSE. The pupils of all of the animals were examined under direct bright illumination both before and after treatment. When the pupils were observed approximately 30 minutes after treatment, it could be easily seen that the treated pupils of animals suffering from BSE were more dilated than the treated pupils of healthy animals.

Preferred diagnostic regimes permit the differences in dilation between healthy and BSE afflicted animals to be readily observed. Accordingly, where tropicamide is used, dosages of 1% tropicamide below 500–600 μl are preferred, so long as the dosage is adequate induce an observable difference in dilation. Those skilled in the art will be able to determine appropriate diagnostic dosages.

Automated Instruments and Systems Suitable for Measuring Pupil Size

A variety of non-invasive automated apparatus is known and commercially available which can be used (or modified for use) in the method of the invention. Preferably, the apparatus used can perform the following functions.

(1) continuous monitoring of pupil size over time;

(2) repetitive measurement of pupil size for periods ranging from less than 1 second to about 5 minutes in duration; and (3) cumulative recording each measurement of pupil size diameter obtained over time.

A number of automated instruments can be used as is or modified for use in the method of the invention. Examples of conventional apparatus for the measurement of pupil size are described in U.S. Pat. Nos. 4,755,043; 5,187,5067; and 4,850,691. In addition, there is a varied class of instruments for measuring pupil diameter which are generally termed "pupillometers." A typical pupillometer measures, displays, and records pupil size before and after a light stimulus causes a constriction and re-dilation of the pupil. These instruments can be modified to eliminate the use of light stimuli to constrict and/or dilate the pupil artificially; and can also be modified to extend the typical manner of usage from making a single measurement to making repetitive measurements over a selected time duration in an uninterrupted manner.

In the method of the invention the size of the pupil along the vertical axis is measured. This is because the size of cow's pupils along the horizontal axis does not change significantly. Thus, a measurement along the vertical axis alone provides a measure of pupil size.

The commercially available Series 4000 eye movement measurement system (Applied Science Laboratories, Bedford, Mass.) can be adapted for use in the method of the invention. This measurement system is an advanced eye tracker, unobtrusively measuring point of gaze and pupil diameter with sophisticated data recording and processing capabilities. A TV camera with a telephoto lens (pupil camera) is directed at one of the subject's eyes. A collimated, near infrared light source that is beamed coaxially with the pupil camera illuminates the eye. A second TV camera (locating camera) provides a wide angle view of the head to simplify locating the eye. The pupil camera, locating camera, and light source are all enclosed in a single housing called the optical head which can be located up to 230 cm from the eye. Sixty individual measurements can be made each second; and a 30 second viewing duration of the pupil will yield 1800 individual data measurements for the single viewing occasion. The video data is pre-processed, digitized, and sent to an attached computer by the electronics unit as it comes from the camera. For use in the method of the invention, this instrument should be adapted to measure pupil area.

Other desirable apparatuses for continuously monitoring pupil size, for repetitively measuring pupil size, and cumulatively recording measurement data over time in an uninterrupted manner are the commercially available Pupillometer systems (Applied Science Laboratories, Bedford, Mass.). These instruments and systems are suited for practicing the present methodology. The pupillometer apparatus provides accurate, real-time measurement and display of pupil size. The pupil is continuously monitored and pupil dimensions are shown directly on a panel meter and also in digital and analog forms. Measurement is also independent of eye movement and other variations over a large field of view. Whereas the TV pupillometer offers accuracy, maximum system flexibility, and high sampling speed, the clinical and field system devices offer simplicity of use, portability, and automatic data recording and display. These devices are well-suited for studies primarily concerned with pupillary reflex function.

The above-described measurement systems are commonly used with human subjects. It may be desirable to use a somewhat modified system for the methods of the invention. One suitable instrument would include a hand held video camera/illuminator and a video monitor both of which are connected to a control unit which is connected to a personal computer. The video camera/illuminator would be held 12 to 24 inches from the eye being measured. The operator would observe the image bing recorded on the monitor to determine whether the pupil is in focus. The monitor would display indicators to show when the cow's pupil is properly recognized. The indicators could include an outline drawn around the pupil or cross hairs indicating the center of the pupil, or both. When the focus is correct and the pupil is properly recognized, measurements are made at a rate of 20 or more readings each second. The measurements can be stored and manipulated.

OTHER EMBODIMENTS

In another embodiment, the pupil constriction velocity in response to stimulation by visible light can be used as a diagnostic indicator for BSE. This method relies measurement of pupil constriction velocity upon exposure to photostimulating visible light of predetermined after the administration of a cholinergic antagonist. In this method the cholinergic antagonist is administered at a dosage which does not cause a substantial change in light stimulated pupil constriction velocity in cows which are not afflicted with BSE. In this method, pupil constriction velocity can be measured using any suitable device. Of course, because the velocity of light stimulated pupil constriction is being measured, the device must be capable of carrying out rapid, repeated measurement of pupil size. Preferred devices are those capable of measuring pupil size at least 10 or more times in a second. Suitable devices include Series 1050 TV Pupillometer from Applied Science Laboratories. The PUPILSCAN™ System, also from Applied Science Laboratories, is also suitable.

In this method, light stimulated pupil constriction velocity is measured on at least two occasions—before treatment with a cholinergic antagonist and after treatment with a cholinergic antagonist. As with the methods described above, the measurement made after treatment is made at a time when the difference in response between BSE afflicted cows and cows not afflicted with BSE. In general, BSE afflicted cows will exhibit a greater change in light stimulated constriction upon treatment with the cholinergic antagonist than cows which are not afflicted with BSE.

What is claimed is:

1. A method for diagnosing the presence or absence of bovine spongiform encephalopathy in a subject cow comprising:

(a) administering to an eye of said subject cow a dose of a mydriatic agent, said dose being insufficient to cause substantial pupil dilation when administered to a cow that is not afflicted with bovine spongiform encephalopathy;

(b) measuring the dilation the pupil of an eye of said subject cow to establish a baseline dilation;

(c) after sufficient time has elapsed for said dosage of said mydriatic agent to cause a change in pupil dilation, measuring the dilation of the pupil of said eye to which said mydriatic agent was administered;

(d) diagnosing the presence or absence of bovine spongiform encephalopathy in said subject cow based on the presence or absence of a change in pupil dilation from said baseline which is characteristic of bovine spongiform encephalopathy.

2. A method for diagnosing the presence or absence of bovine spongiform encephalopathy in a subject cow comprising:

(a) administering to an eye of said subject cow a dose of a miotic agent, said dose being insufficient to cause substantial pupil constriction when administered to a cow that is not afflicted with bovine spongiform encephalopathy;

(b) measuring the dilation the pupil of an eye of said subject cow to establish a baseline dilation;

(c) after sufficient time has elapsed for said dosage of said miotic agent to cause a change in pupil constriction, measuring the constriction of the pupil of said eye to which said miotic agent was administered;

(d) diagnosing the presence or absence of bovine spongiform encephalopathy in said subject cow based on the presence or absence of a change in pupil constriction from said baseline which is characteristic of bovine spongiform encephalopathy.

* * * * *